United States Patent [19]

Bauer et al.

[11] 4,379,458
[45] Apr. 12, 1983

[54] TROCAR SLEEVES HAVING A BALL VALVE

[75] Inventors: Siegfried Bauer, Heidelsheim; Manfred Boebel, Oetisheim, both of Fed. Rep. of Germany

[73] Assignee: Richard Wolf GmbH, Knittlingen, Fed. Rep. of Germany

[21] Appl. No.: 168,070

[22] Filed: Jul. 14, 1980

Related U.S. Application Data

[62] Division of Ser. No. 959,561, Nov. 13, 1978, Pat. No. 4,233,982.

[51] Int. Cl.³ .......................... A61B 17/34; A61M 5/00
[52] U.S. Cl. ..................................... 604/264; 128/754; 604/905
[58] Field of Search .................... 128/349, 347, 350 R, 128/350 V, 4, 214.4, 754, 756; 251/149.2, 149.3; 27/24 A

[56] References Cited

U.S. PATENT DOCUMENTS

| | | | |
|---|---|---|---|
| 1,497,054 | 7/1924 | Allabach | 251/149.2 |
| 1,818,508 | 9/1931 | Scott | 251/149.2 |
| 1,858,766 | 5/1932 | Dabroski | 251/149.2 |
| 2,641,485 | 6/1953 | Dupuy | 251/149.2 |
| 3,055,370 | 9/1962 | McKinney et al. | 128/754 |
| 3,288,142 | 10/1966 | Hakin | 128/350 V |
| 3,730,216 | 4/1973 | Arnett et al. | 251/149.2 |
| 3,754,564 | 9/1973 | Naumburg et al. | 251/149.2 |
| 3,768,102 | 11/1973 | Kwan-Gett et al. | 128/349 R |
| 3,897,810 | 8/1975 | Arnett et al. | 251/149.2 |
| 3,911,977 | 10/1975 | Berger | 251/149.2 |
| 4,007,909 | 2/1977 | Buseth et al. | 251/149.2 |
| 4,245,635 | 1/1981 | Kontos | 128/214.4 |
| 4,261,357 | 4/1981 | Kontos | 128/214.4 |

FOREIGN PATENT DOCUMENTS

| | | | |
|---|---|---|---|
| 201293 | 3/1908 | Fed. Rep. of Germany | 251/149.3 |
| 1267377 | 12/1968 | Fed. Rep. of Germany | 128/4 |
| 2284303 | 1/1976 | France | 128/4 |

*Primary Examiner*—Michael H. Thaler
*Assistant Examiner*—C. W. Shedd
*Attorney, Agent, or Firm*—Kinzer, Plyer, Dorn & McEachran

[57] ABSTRACT

A trocar sleeve of the kind having a widened part forming a housing between the distal portion of the sleeve and its proximal portion, which latter extends from a plug for the widened housing part, and a ball valve in the widened housing part which ball valve is closable by resilient means and which is openable by a trocar passing through the sleeve.

In this invention, the widened part forming the housing receives an insert of U-shaped cross-section which is securable to the plug to stress an inserted sealing gasket of deformation-resistant plastics material which is to be drilled through to form a valve seating. The space in the U formed by the insert forms a space for the ball of the ball valve to move in, the ball, before the insert is screwed to the plug, being connected to a shaft insertable in the insert and carrying a tangentially loaded helical spring and being placed under stress by connecting the insert to the plug.

1 Claim, 5 Drawing Figures

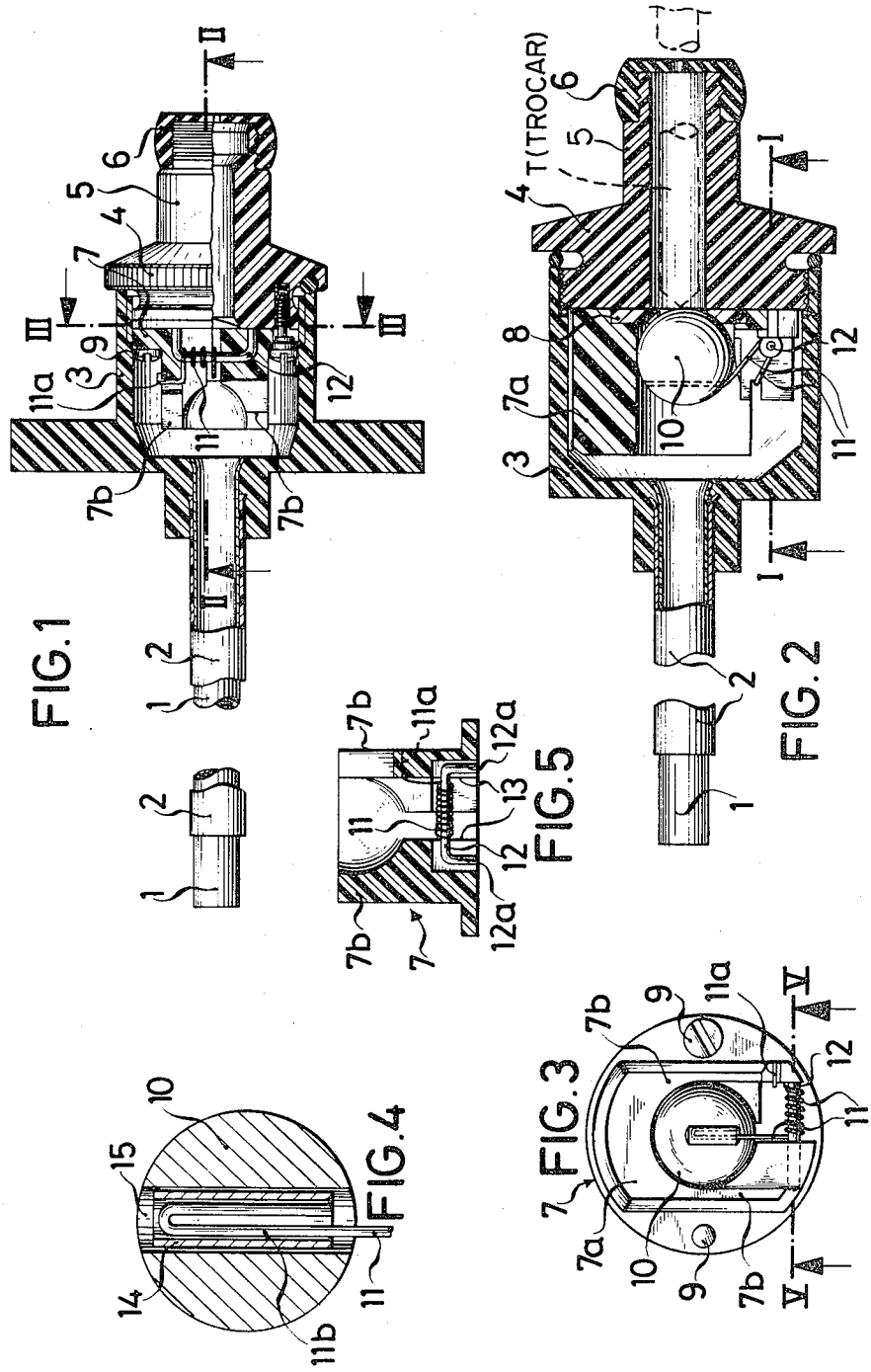

TROCAR SLEEVES HAVING A BALL VALVE

This is a division of application Ser. No. 959,561, filed Nov. 13, 1978, now U.S. Pat. No. 4,233,982.

BACKGROUND OF THE INVENTION

This invention relates to trocar sleeves (sometimes referred to as cannuli), of the kind having a widened part forming a housing between the distal portion of the sleeve and its proximal portion, which latter extends from a plug for the widened housing part, and a ball valve in the widened housing part which ball valve is closable by resilient means and which is openable by a trocar passing through the sleeve. Hereinafter such a trocar sleeve will be referred to as "of the kind described".

It is known to provide trocar sleeves or cannuli between their proximal and distal portions with a widened part which forms a housing and in which a magnetic flap valve is resiliently mounted, as described in German Gebrauchsmuster No. 7 430 345 and British Pat. No. 1482857, so that the sleeve be sealed after the trocar has been withdrawn and in this way any escape of gas from say, an abdominal cavity, can be prevented. Practical experience has shown that after a given period of time an arrangement of this kind no longer performs its appointed function.

It is also known as described in German Auslegeschrift No. 1 267 377 to fit, in the widened proximal part of the sleeve, a ball valve whose ball is pressed against a valve seating by a tangentially loaded helical spring but is able to move aside when the trocar or an instrument is passed through. This known design results in the sleeve having an eccentrically projecting widened portion and is expensive.

It is an object of the invention to simplify the construction of a ball valve and its fitting to a trocar sleeve of the kind described, with the valve seating accurately aligned, and to reduce manufacturing costs while providing a long life.

SUMMARY OF THE INVENTION

Accordingly, the invention consists in a trocar sleeve of the kind described, wherein the widened part forming the housing receives an insert of U-shaped cross-section and which may be made from a plastics material, which is screwable to the plug to stress an inserted sealing gasket of deformation-resistant material which also may be a plastics material and which is to be drilled through to form a valve seating, and wherein the space in the U formed by the insert forms a space for the ball of the ball valve to move in, and which ball, before the insert is screwed to the plug, is connected to a shaft insertable in the insert and carrying a tangentially loaded helical spring and is placed under stress by connecting the insert to the plug.

By this means it is possible to stress the sealing gasket of deformation-resistant material and press it firmly into place, while sealing off the internal passage, when U-shaped insert is screwed to the plug carrying the proximal portion of the sleeve, and then to drill it out through the proximal portion of the sleeve to the requisite inside diameter by means of a stepped drill, thus obtaining an absolutely central bore in the gasket and a satisfactory seating for the ball of the valve. A tangentially loaded helical spring which is free to move is freely inserted in the U-shaped insert connected to the plug and is held secure by the way in which it fits into the insert. The inert is then screwed up to the plug and the drilled out valve seating, as stated above, by which means the helical spring is placed under stress. The plug, together with the U-shaped insert, is then screwed into the widened part forming the housing.

The fitting of the spring mounting for the ball of the valve is particularly facilitated if, in a further embodiment, the ball of the ball valve is provided with a transverse groove opposite the valve seating, for a flat tube secured in the groove to receive a tangential portion of the helical spring which is bent into a hair-pin shape and which is connected at its free end to the tube, the turns of the spring enclosing the central section of an arch-shaped shaft which is inserted in recesses parallel to the axis of the insert in the side-pieces of the U-shaped insert on the side adjacent the plug, the other tangential portion of the spring being supported in one of the side-pieces of the U-shaped insert.

BRIEF DESCRIPTION OF THE DRAWING

In order that the invention may be more clearly understood, reference will now be made to the accompanying drawings which show one embodiment thereof by way of example and in which:

FIG. 1 is an axial section through the proximal part of a trocar sleeve with an interrupted side-view of the distal part thereof, FIG. 2 is an axial section of the sleeve, viewed at right angles to FIG. 1, FIG. 3 is an end-on view of the insert looking from line III—III of FIG. 1, FIG. 4 is an enlarged scale end-on view of the side of the ball of the ball valve opposite the valve seating, FIG. 5 is a section through the insert on line V—V of FIG. 2 or 3.

DETAILED DESCRIPTION OF PREFERRED EMBODIMENT

Referring now to the drawings, a metal trocar sleeve 2, (also referred to in the art as a trocar cannula) which is provided with an internal tubular insert 1 of insulating plastics material, is firmly connected at the proximal end to a widened part 3 forming a housing which can be closed off by a screw-in plug 4 carrying the proximal portion 5 of the sleeve. The housing part 3, the plug 4 and portion 5 of the sleeve likewise consist of a suitable plastics material in this embodiment. Portion 5 of the sleeve is provided with a rubber cap 6 having a central aperture to provide sealed passage for a trocar, a telescope, an endoscope or instruments.

To seal off the trocar sleeve 1, 2 after the trocar or the instruments have been withdrawn, a ball valve is fitted in the widened housing part 2.

In this embodiment this valve comprises an injection-moulded plastics insert 7 of U-shaped cross-section perpendicular to the axis of the sleeve. On the plug side, the insert 7 is provided with a circular recess for the insertion of a sealing gasket 8 (FIG. 2) of heat-resistant and deformation-resistant material, such as a suitable plastics material, which can be pressed firmly into place under stress and while sealing off the internal passage, by connecting the insert 7 to the plug 4 by means of screws 9. After parts 7 and 4 have been screwed together, the sealing gasket 8 is provided with an exactly central bore of the requisite diameter by means of a stepped drill guided in portion 5 of the sleeve, and the resulting sealing ring then acts as a valve seating for the ball of a ball valve.

Before the valve-sealing ring 8 is finally tightened down, or in other words before the insert 7 is finally connected to the plug 4, a unit consisting of a valve-ball 10 and a tangentially loaded helical spring 11 carried on an arch-shaped shaft 12 is inserted in the insert 7. For this purpose the side-pieces 7b of the insert 7 are provided on the side adjacent the plug 4 with recesses 13 parallel to the axis of the insert into which are fitted the side-sections 12a of the arch shaped shaft 12, onto whose central section the turns of the torsion spring 11 have been slid. One end 11a of the spring is hooked into a notch in one side-piece 7b of the U (FIGS. 1, 3 and 5) and the other end 11b of the spring, which is bent into a hair-pin shape, is inserted in a flat tube 14 which is secured in a transverse groove 15 in the valve-ball 10 on the side remote from the plug 4 (FIG. 4). The free end of the hair-pin portion 11b is solidly connected to the tube 14, by welding for example.

In this way the valve-ball 10, together with its spring mounting 11 and the shaft 12 for the spring, is connected to the insert 7 while being free to move and is held fast in the insert 7, the spring being relaxed initially. Then, after the valve seating ring 8 has been inserted, the insert 7, together with the spring and the valve-ball, is screwed to the plug and at the same time the helical spring 11 is thus placed under stress, by which means the valve ball 10 is brought to bear against the valve seating 8.

The plug 4, together with the complete valve insert 7, is then screwed to the widened housing part 3 and fitting is thus complete.

To perforate the wall of a patient's abdomen, a trocar is pushed through the trocar sleeve or cannula so produced and lifts the valve ball off the seating and forces it aside, the sealing function then being taken over by the rubber cap 6 and the ball 10 being allowed a limited amount of movement on the hair-pin shaped tangential portion 11b of the spring 11, any damage to the valve-ball 10, which in any case is only subject to point or line contact, being largely obviated by its withdrawing movement and any breakage of the spring at the ends of its tangenial portions being virtually impossible.

We claim:

1. A hollow surgical trocar sleeve instrument adapted to be inserted into the abdomen to enable another surgical instrument to be passed therethrough into the abdomen of the patient, and comprising an outer cylindrical metal sleeve and an inner concentric insulating plastic sleeve joined to one another in concentric relation, the tip of the inner insulating plastic sleeve extending considerably beyond the tip of the outer metal sleeve so that there is a sleeve portion of insulating plastic material in front of the tip of the metal sleeve without there being metal at the distal tip of the trocar instrument, a one-piece plastic housing joined to the rear of the outer metal sleeve, said housing supporting at the proximal end a seal cap of resilient material having a central aperture therethrough aligned to the bore of the inner plastic sleeve for capturing the other instrument by a seal fit when passed therethrough.

* * * * *